United States Patent
Farris et al.

(10) Patent No.: US 11,684,726 B2
(45) Date of Patent: Jun. 27, 2023

(54) INJECTION NEEDLE INSERTION MECHANISM FOR INJECTOR

(71) Applicant: West Pharma. Services IL, Ltd., Ra'anana (IL)

(72) Inventors: Jason W. Farris, Gilbert, AZ (US); Samuel Dauphinais, Scottsdale, AZ (US); Ran Hezkiahu, Heizliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 433 days.

(21) Appl. No.: 16/648,398

(22) PCT Filed: Sep. 21, 2018

(86) PCT No.: PCT/IB2018/001164
§ 371 (c)(1),
(2) Date: Mar. 18, 2020

(87) PCT Pub. No.: WO2019/058177
PCT Pub. Date: Mar. 28, 2019

(65) Prior Publication Data
US 2020/0261658 A1    Aug. 20, 2020

Related U.S. Application Data

(60) Provisional application No. 62/631,079, filed on Feb. 15, 2018, provisional application No. 62/561,386, filed on Sep. 21, 2017.

(51) Int. Cl.
*A61M 5/142* (2006.01)
*A61M 5/32* (2006.01)
(Continued)

(52) U.S. Cl.
CPC .... *A61M 5/31585* (2013.01); *A61M 5/14248* (2013.01); *A61M 5/31526* (2013.01);
(Continued)

(58) Field of Classification Search
CPC .......... A61M 5/31585; A61M 5/14248; A61M 5/31526; A61M 5/3286;
(Continued)

(56) References Cited

U.S. PATENT DOCUMENTS

| 5,865,804 A | 2/1999 | Bachynsky |
| 2016/0199590 A1* | 7/2016 | Schabbach .......... A61M 5/3287 604/240 |

(Continued)

FOREIGN PATENT DOCUMENTS

| CN | 101631585 A | 1/2010 |
| CN | 103874460 A | 6/2014 |

(Continued)

OTHER PUBLICATIONS

Int'l Search Report and Written Opinion dated Jan. 1, 2019 in Int'l Application No. PCT/IB2018/001164.

(Continued)

*Primary Examiner* — Kevin C Sirmons
*Assistant Examiner* — Avery Smale
(74) *Attorney, Agent, or Firm* — Blank Rome LLP

(57) ABSTRACT

An injector includes a needle movable from a retracted position to an injection position. A rotary biasing assembly is stabilized in a stored energy state and releasable into an energy releasing state and includes a cam. A cam follower couples the rotary biasing assembly with the needle and is configured to transform rotation of the rotary biasing assembly in the energy releasing state thereof into translation of the needle from the retracted position to the injection position. An activation switch is rotatable from an unactivated position, stabilizing the rotary biasing assembly in the stored energy state thereof, to an activated position, releasing the rotary biasing assembly into the energy releasing state thereof. An activation button is movably mounted to (Continued)

the injector housing and is translatable from an unactuated position to an actuated position, whereby the translation rotates the activation switch from the unactivated position to the activated position thereof.

19 Claims, 9 Drawing Sheets

(51) Int. Cl.
*A61M 5/158* (2006.01)
*A61M 5/315* (2006.01)

(52) U.S. Cl.
CPC . *A61M 5/3286* (2013.01); *A61M 2005/14252* (2013.01); *A61M 2005/1585* (2013.01)

(58) Field of Classification Search
CPC ........... A61M 2005/14252; A61M 2005/1585; A61M 2005/208; A61M 2005/1581; A61M 2005/14284; A61M 5/14244; A61M 5/14276; A61M 2005/14272; A61M 2005/1586; A61M 5/3287
See application file for complete search history.

(56) References Cited

U.S. PATENT DOCUMENTS

| 2016/0213840 A1* | 7/2016 | Schabbach | A61M 5/3287 |
| 2017/0182303 A1* | 6/2017 | Tallarida | A61M 39/0208 |
| 2017/0354788 A1* | 12/2017 | Quinn | A61M 5/32 |

FOREIGN PATENT DOCUMENTS

| CN | 105517593 A | 4/2016 |
| CN | 106029127 A | 10/2016 |
| WO | 2006108809 A1 | 10/2006 |
| WO | 2013036602 A1 | 3/2013 |
| WO | 2015032745 A1 | 3/2015 |
| WO | 2015070914 A1 | 5/2015 |
| WO | 2017127215 A1 | 7/2017 |
| WO | 2018070978 A1 | 4/2018 |

OTHER PUBLICATIONS

Int'l Preliminary Report on Patentability dated Feb. 26, 2020 in Int'l Application No. PCT/IB2018/001164.

* cited by examiner

INJECTION NEEDLE INSERTION MECHANISM FOR INJECTOR

CROSS-REFERENCE TO RELATED APPLICATIONS

This application is a Section 371 of International Application No. PCT/IB2018/001164, filed Sep. 21, 2018, which was published in the English language on Mar. 28, 2019, under International Publication No. WO 2019/058177 A1, which claims the benefit of priority under 35 U.S.C. § 119(e) to U.S. Provisional Patent Application No. 62/561,386, titled "Oblique Ratchet Switch For Needle Insertion", filed on Sep. 21, 2017, and U.S. Provisional Patent Application No. 62/631,079, titled "Rotating Needle Insertion Switch", filed on Feb. 15, 2018, the entire contents of each of which are incorporated herein by reference in their entirety.

BACKGROUND OF THE DISCLOSURE

The present disclosure is generally directed to an injection needle insertion mechanism for an injector.

Conventional wearable injectors may lock an injection needle in a retracted state, wherein the needle tip is contained within the injector, prior to use. Such injectors may also drive the injection needle into an injection position, wherein the needle tip penetrates the skin surface of a recipient (user or patient), during use. Driving of the injection needle is often implemented by a driving mechanism including a needle insertion spring.

One drawback of such conventional devices is that the geometry of the components of the injector locking the injection needle in the retracted position are often exposed to the full force of the needle insertion spring, preventing the spring from driving the injection needle into the injection position thereof. Such design introduces a risk of damage to the injector due to plastic creep of the locking mechanism components during storage, among other reasons. Moreover, the locking mechanism components risk binding to one another due to the relatively high forces thereon and friction therebetween.

Therefore, it would be advantageous to manufacture an injector having a design wherein the locking mechanism components are not subjected to the full force of the driving mechanism during storage of the device, thereby minimizing the risk of creep and binding.

BRIEF SUMMARY OF THE DISCLOSURE

Briefly stated, one aspect of the present disclosure is directed to an injector. The injector includes an injector housing having a base housing portion defining a skin contact surface and a chassis attached to the base housing portion. An injection needle is supported by the chassis and movable with the chassis relative to the base housing portion from a retracted position, wherein at least a tip of the injection needle is contained within the base housing portion, to an injection position, wherein at least the tip of the injection needle protrudes from the base housing portion. At least one rotary biasing assembly is stabilized in a stored energy state and is releasable into an energy releasing state. The at least one rotary biasing assembly includes a cam. At least one cam follower corresponding to the at least one rotary biasing assembly couples the at least one rotary biasing assembly with the injection needle and is configured to transform rotation of the at least one rotary biasing assembly in the energy releasing state thereof into translation of the chassis and the injection needle, relative to the base housing portion, from the retracted position to the injection position. An activation switch is coupled with the chassis and rotatable from an unactivated position, stabilizing the at least one rotary biasing assembly in the stored energy state thereof, to an activated position, releasing the at least one rotary biasing assembly into the energy releasing state thereof. An activation button is movably mounted to the injector housing and is translatable from an unactuated position to an actuated position. Translation of the activation button from the unactuated position to the actuated position rotates the activation switch from the unactivated position to the activated position thereof.

Another aspect of the present disclosure is directed to an injector including an injector housing having a base housing portion defining a skin contact surface. An injection needle is supported by the injector housing, the injection needle being movable relative to the base housing portion from a retracted position, wherein at least a tip of the injection needle is contained within the base housing portion, to an injection position, wherein at least the tip of the injection needle protrudes from the base housing portion. At least one rotary biasing assembly is stabilized in a stored energy state and is releasable into an energy releasing state. The at least one rotary biasing assembly includes a cam. At least one cam follower corresponding to the at least one rotary biasing assembly couples the at least one rotary biasing assembly with the injection needle and is configured to transform rotation of the at least one rotary biasing assembly in the energy releasing state thereof into translation of the injection needle, relative to the base housing portion, from the retracted position to the injection position. An activation switch is rotatable from an unactivated position, stabilizing the at least one rotary biasing assembly in the stored energy state thereof, to an activated position, releasing the at least one rotary biasing assembly into the energy releasing state thereof. An activation button is movably mounted to the injector housing and is translatable from an unactuated position to an actuated position, wherein translation of the activation button from the unactuated position to the actuated position rotates the activation switch from the unactivated position to the activated position thereof.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Figure 1:
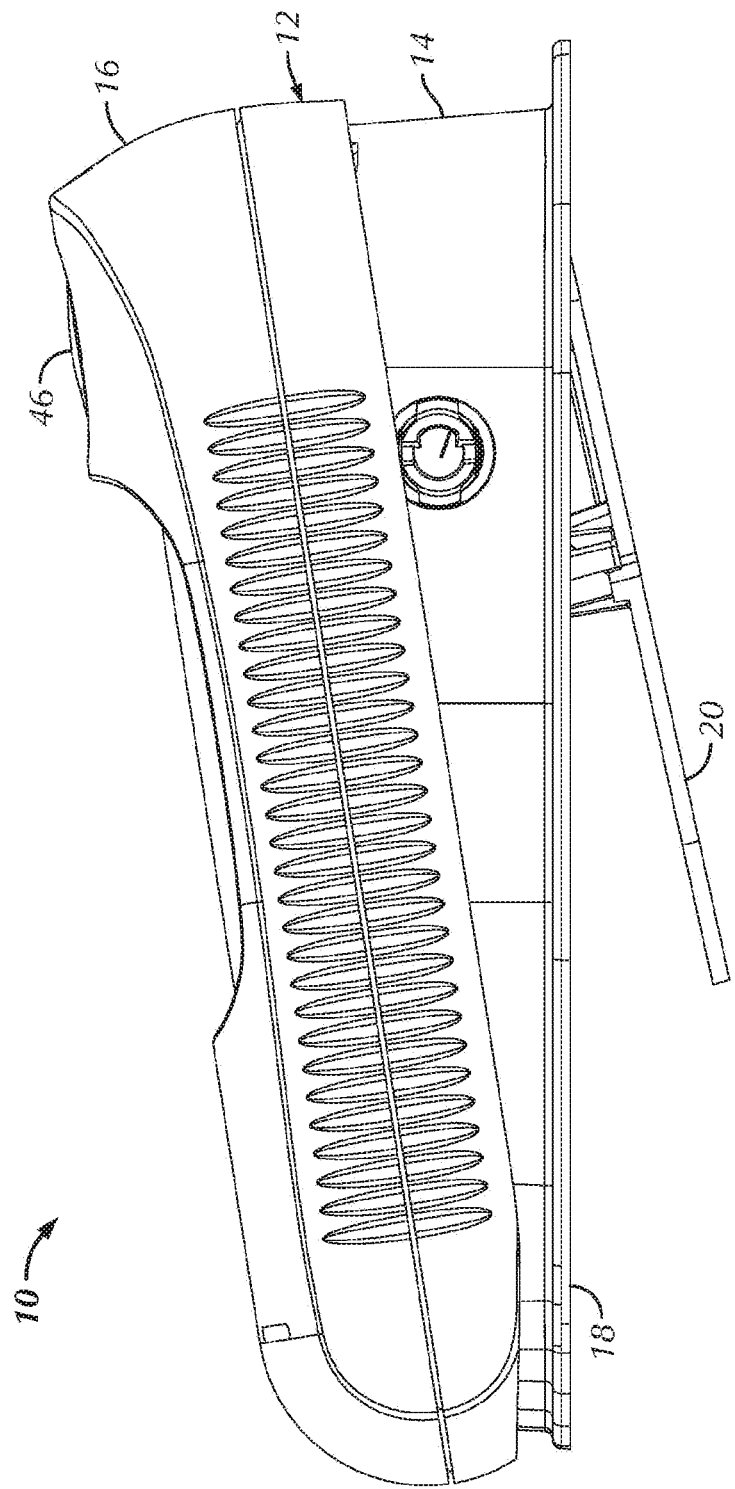
FIG. 1 is a side elevational view of an injector in accordance with an embodiment of the present disclosure, with an injection needle of the injector in a retracted position.
Figure 2:
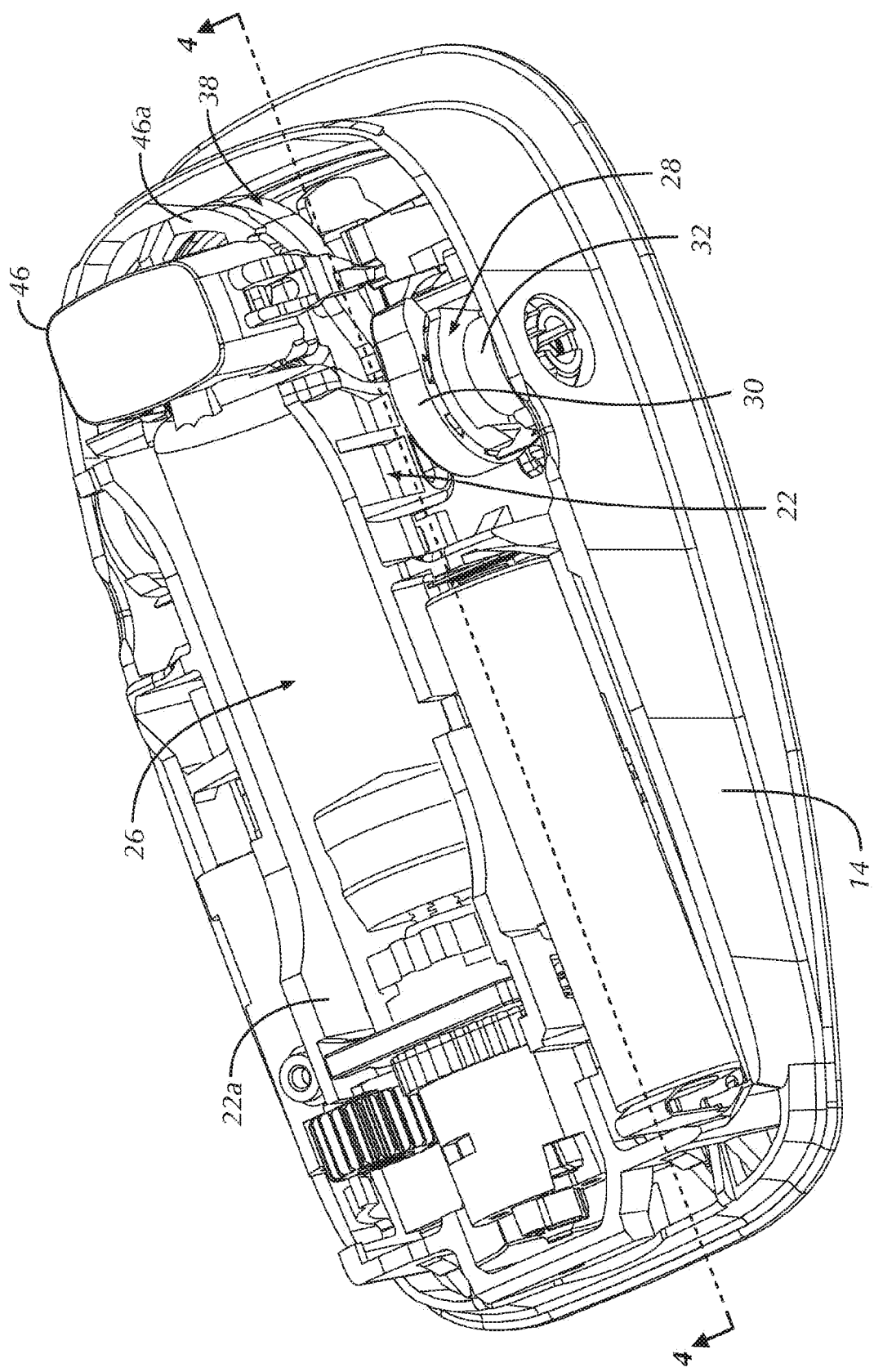
FIG. 2 is a rear, top and side perspective view of the injector of FIG. 1, with a cover housing portion thereof removed to show internal components within the injector.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-9 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. The injector 10 generally includes an injector housing 12 having a base housing portion 14 and a cover housing portion 16 (FIG. 1) upon the base housing portion 14 and movably attached, e.g., pivotably, relative thereto. The base housing portion 14 includes a surface 18 configured to contact a skin surface of a user (not shown), e.g., a patient, the surface 18 having an opening 18a (FIG. 4) therein. In the illustrated embodiment, the skin contacting surface 18 defines a base surface of the injector housing 12, but the disclosure is not so limited. In some embodiments, the injector 10 may include a safety latch 20 (FIG. 1) pivotably attached to the base housing portion 14, and movable between a first position and a second position. In the first position (FIGS. 6, 7), the safety latch 20 extends generally flush with the skin contacting surface 18 of the injector 10, but the disclosure is not so limited. In the second position (FIGS. 1, 2), the safety latch 20 is pivoted away, i.e., downwardly, from the skin contacting surface 18.

A chassis 22, constructed, for example, from a polymeric or metal material, combinations thereof, or the like, is mounted within the injector housing 12, i.e., between the cover housing portion 16 and the base housing portion 14, and movably attached to the base housing portion 14. In the illustrated embodiment, the chassis 22 is pivotably attached to the base housing portion 14 proximate a rear end of the chassis 22 and the base housing portion 14, but the disclosure is not so limited. An injection needle 24 is supported within the injector housing 12 by the chassis 22. In the illustrated embodiment, the chassis 22 defines a cartridge slot 22a configured, i.e., shaped and sized, to receive a cartridge 26 usable with the injector 10 thereon. Optionally, the cartridge slot 22a cradles the cartridge 26.

One non-limiting example of the cartridge 26 is described in International Patent Application Publication No. WO 2017/062931, entitled "Bent Fluid Path Add On to a Prefilled Fluid Reservoir", the entire contents of which are incorporated by reference herein. As shown best in FIG. 5, the injection needle 24 extends from a front end of the cartridge 26, and bends approximately 90° relative to a longitudinal axis of the cartridge 26, but the disclosure is not so limited. Alternatively, the injection needle 24 may be indirectly or directly secured to the chassis 22 and fluidly connectable to the cartridge 26 upon insertion of the cartridge 26 in the cartridge slot 22a. The injection needle 24 is movable along with the chassis 22 relative to the base housing portion 14 from a retracted position (shown best in FIG. 4), wherein at least a tip of the injection needle 24 is contained within the base housing portion 14, to an injection position (FIGS. 6, 7), wherein at least the tip of the injection needle 24 protrudes from the base housing portion 14 through the opening 18a in the surface 18 and into the skin of a user (not shown).

To move the chassis 22 relative to the base housing portion 14, the injector 10 includes at least one rotary biasing assembly 28 stabilized in a stored energy state and releasable into an energy releasing state. As should be understood by those of ordinary skill in the art, the stored energy state of the rotary biasing assembly 28 is a state in which the biasing assembly 28 stores at least some potential energy. The energy releasing state of the rotary biasing assembly 28 is a state of the biasing assembly 28 in which the biasing assembly 28 releases at least some of the previously stored potential energy from the stored energy state. In the illustrated embodiment, the injector 10 includes two rotary biasing assemblies 28 (one on each side of the chassis 22), but the disclosure is not so limited. For the sake of brevity, the remaining description will be directed to one rotary biasing assembly 28, but is substantially equally applicable to each rotary biasing assembly 28 of the injector 10.

The rotary biasing assembly 28 includes a drive wheel 30 having a toothed interior ratchet surface 30a and a pawl 30b engaged with the toothed ratchet surface 30a (FIG. 4) and having a shaft 30c extending therefrom. A torsion spring 32 is wound around the shaft 30c, thereby being rotatably coupled with the pawl 30b, and, in turn, the drive wheel 30. As should be understood by those of ordinary sill in the art, the pawl 30b and the toothed ratchet surface 30a are configured to effect rotation of the drive wheel 30 in a single rotational direction (e.g., clockwise as seen from the perspective shown in FIGS. 4, 8), and prevent rotation of the drive wheel 30 in the opposing rotational direction. As also should be understood, rotational force of the drive wheel 30 (FIG. 8: torque T1) is a product of, at least, in part, the spring force (torsion coefficient) of the torsion spring 32. In the stored energy state of the rotary biasing assembly 28, the torsion spring 32 is wound (at least partially) and prevented from unwinding relative to the wound state thereof (as will be explained in further detail below). The torsion spring 32 is configured to unwind (relative to the stored energy state) in the energy releasing state. As should be understood by those of ordinary skill in the art, the rotary biasing assembly 28 may alternatively take the form of, or include, other members capable of storing and releasing energy. Non-limiting examples include other springs (e.g., coil or leaf springs), elastic bands, and the like, configured to perform the function of the torsion spring 32 and/or the entire rotary biasing assembly 28 described herein.

Figure 3:
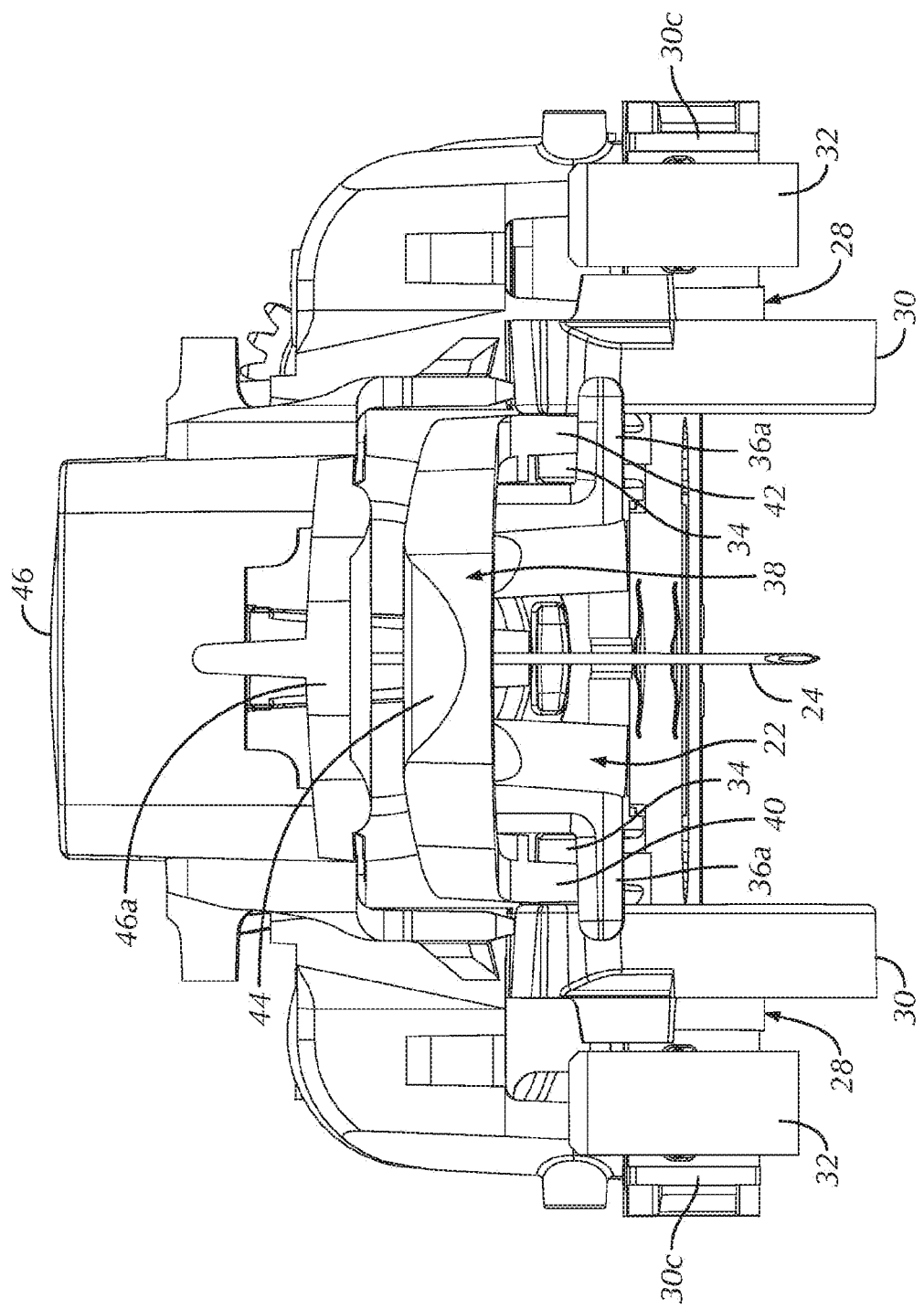
FIG. 3 is a front elevational view of a chassis, activation switch, activation button and rotary driving assemblies of the injector of FIG. 1.
Figure 4:
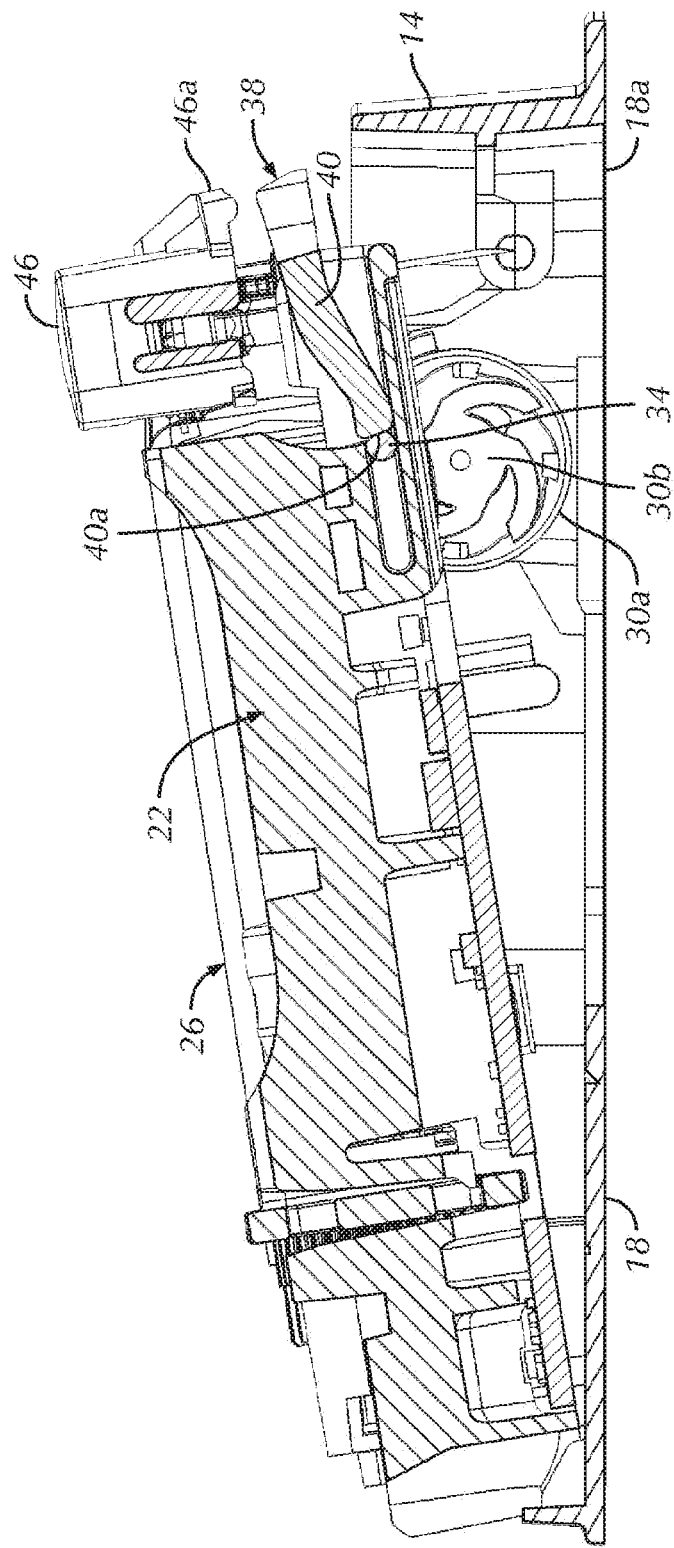
FIG. 4 is a cross-sectional, elevational view of the injector of FIG. 1, taken along the sectional line 4-4 of FIG. 2.
Figure 5:
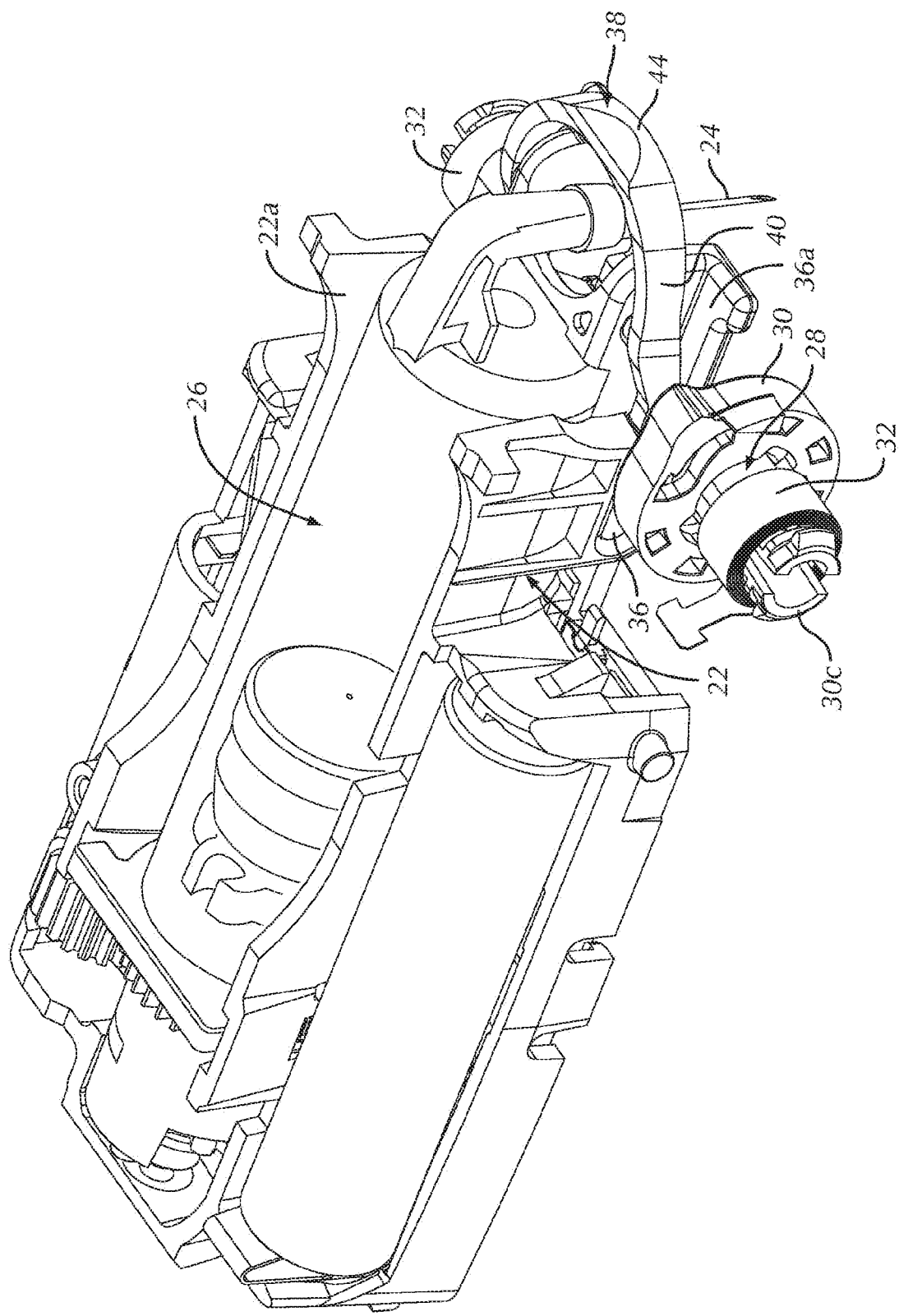
FIG. 5 is a front, top and side perspective view of the chassis, activation switch, activation button and rotary driving assemblies of the injector of FIG. 1.
Figure 6:
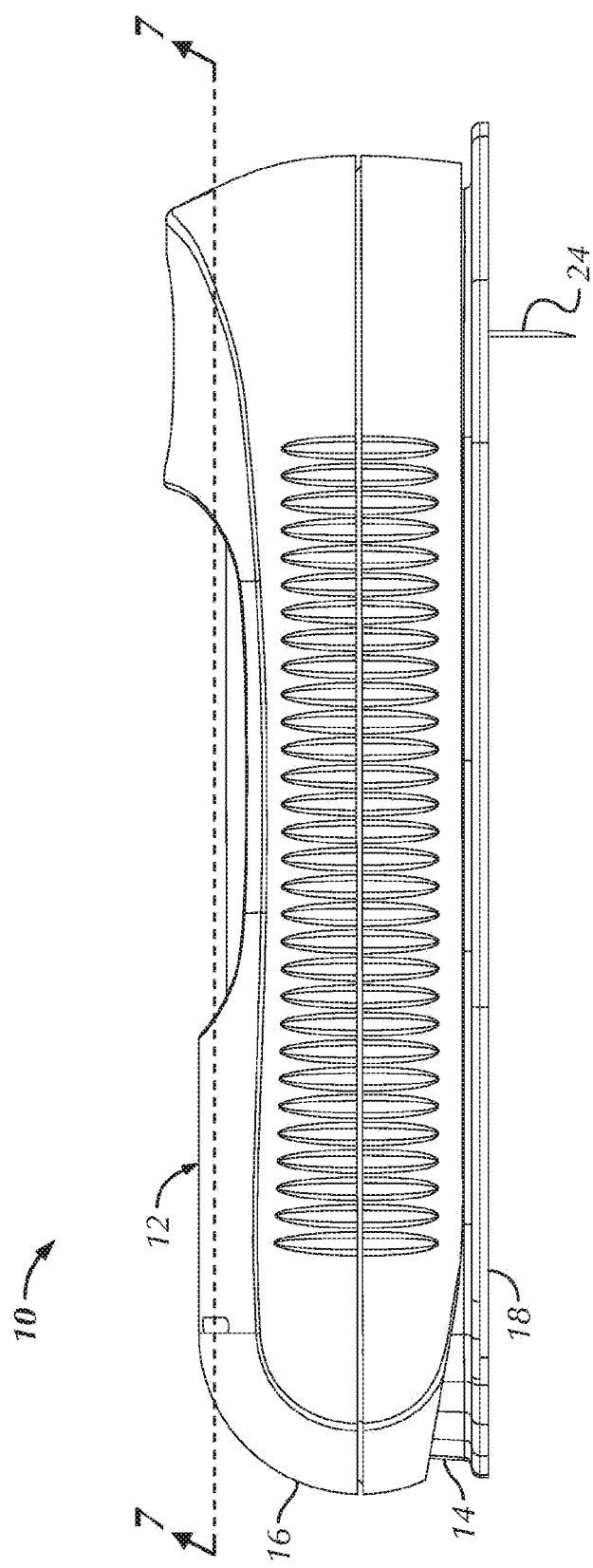
FIG. 6 is a side elevational view of the injector of FIG. 1, with the injection needle in an injection position.

The rotary biasing assembly 28 further includes a cam 34 (FIGS. 3, 4). At least one cam follower 36, corresponding to each cam 34, couples the at least one rotary biasing assembly 28 with the injection needle 24 (as will be described in further detail below). Accordingly, the injector 10 includes two cam followers 36 in the illustrated embodiment, but the disclosure is not so limited. Similarly to the rotary biasing assembly 28, the remaining description will be directed to one cam follower 36, for the sake of brevity, but is substantially equally applicable to each cam follower 36 of the injector 10.

The linkage of the cam 34 with the cam follower 36 is configured to transform/convert rotary motion of the rotary biasing assembly 28 into translation of the chassis 22 and the injection needle 24 from the retracted position thereof to the injection position thereof, relative to the base housing portion 14. In the illustrated embodiment, the cam 34 takes the form of a pin projecting from the drive wheel 30 (as will be explained in further detail below), but the disclosure is not so limited. As should be understood, the cam 34 may take the form of alternative components in a mechanical linkage configured to perform the function of the pin 34 described herein. In the illustrated embodiment, the cam follower 36 takes form of a substantially horizontal and linear slot formed in the side of the chassis 22 facing the drive wheel 30, but the disclosure is not so limited. As non-limiting examples, the slot 36 may alternatively extend in different directions other than horizontally and/or may be non-linear, e.g., curved or have multiple sections angled relative to one another. The pin 34 projects from the drive wheel 30 and into engagement with the slot 36.

Release of the at least one rotary biasing assembly 28 into the energy releasing state rotates the drive wheel 30, including the pin 34. The diameter of the pin 34 and the height of the slot 36 are correspondingly configured, however, to substantially solely permit horizontal sliding of the pin 34 inside and along the slot 36. Accordingly, the engagement/linkage of the pin 34 with the slot 36 decomposes the rotation of the drive wheel 30 into two separate, but linked, motions. That is, the engagement/linkage of the pin 34 with the slot 36 decomposes the rotation of the drive wheel 30 into a horizontal force component H (FIG. 8) sliding the pin 34 along the slot 36 (toward the right in FIG. 8) and a separate vertical force component V (FIG. 8) translating the chassis 22 and, in turn, the injection needle 24 (downwardly in the orientation of FIG. 8), relative to the base housing portion 14 from the retracted position to the injection position, i.e., the needle insertion force. Despite being separate forces/motions, sliding of the pin 34 and translation of the chassis 22 remain linked. That is, prevention of the horizontal sliding of the pin 34 along the slot 36 also prevents rotation of the drive wheel 30 and, in turn, prevents the translation of the chassis 22 and the injection needle 24 from the retracted position to the injection position.

The injector 10 further includes an activation switch 38, constructed, for example, from a polymeric or metal material, combinations thereof, or the like, rotatably coupled with the chassis 22 and rotatable from an unactivated position (shown best in FIG. 4), stabilizing the at least one rotary biasing assembly 28 in the stored energy state thereof, to an activated position (shown best in FIG. 7), releasing the at least one rotary biasing assembly 28 into the energy releasing state thereof. In the illustrated embodiment, the activation switch 38 is pivotably coupled with the chassis 22 proximate a front end of the chassis 22, but the disclosure is not so limited. In the illustrated embodiment, the activation switch 38 takes the form of a generally U-shaped member having a first arm 40, with a terminal free end 40a, an opposing second arm 42 with a terminal free end (not shown) and a central portion 44 extending between the first and second arms 40, 42.

The first arm 40 extends along one side of the chassis 22 and extends, in the unactivated position thereof, toward one slot 36, the second arm 42 extends along an opposing side of the chassis 22 and extends, in the unactivated position thereof, toward another slot 36, and the central portion 44 extends between the first and second arms 40, 42, curving around a front end of the chassis 22. As should be understood, however, the central portion 44 is not limited to a curving portion. At least one of the first and second arms 40, 42 (and both in the illustrated embodiment) is pivotably coupled with the chassis 22, e.g., via a pin connection 41 (see FIG. 8) defining the pivot point of the activation switch 38. For the sake of brevity, the remaining description will be directed to the first arm 40 and the terminal end 40a thereof, but is substantially equally applicable to the second arm 42 of the activation switch 38, and the terminal end of the second arm 42, respectively.

At least one of the terminal ends of the first and second arms 40, 42 abuts the pin 34 in the unactivated position of the activation switch, preventing horizontal sliding of the pin 34 along the slot 36 in the rotational direction of the drive wheel 30, thereby preventing rotation of the drive wheel 30. As shown in FIG. 4, the terminal end 40a of the first arm 40 abuts the pin 34 on one side of the chassis 22. Engagement of the terminal end 40a with the pin 34, therefore, maintains the rotary biasing assembly 28 in the stored energy state thereof. Rotation of the activation switch 38 from the unactivated position into the activated position thereof disengages the terminal end 40a from the pin 34 (FIG. 7), thereby permitting sliding of the pin 34 along the slot 36, and, in turn, releasing the rotary biasing assembly 28 into the energy releasing state thereof, i.e., in the form of unwinding of the torsion spring(s) 32 (relative to the stored energy state), in turn rotating the drive wheel 30. The chassis may include a lip 36a extending laterally from a base end of at least one of the slots 36 (shown best in FIGS. 3, 5) and underlying at least one of the first and second arms 40, 42, blocking unintended rotation of the activation switch 38 from the unactivated position in a direction away from the activated position.

One advantage of the engagement/linkage of the pin 34 with the slot 36, decomposing the rotation of the rotary biasing assembly 28 into separate horizontal and vertical force components is that the activation switch 38 is exposed solely to the horizontal force component H without being exposed to the vertical force component V (the needle insertion force) in order to maintain the rotary biasing assembly 28 in the stored energy state thereof. That is, the terminal end 40a of the activation switch 38 must only absorb and oppose the horizontal force component H applied by the pin 34, decomposed from the rotational force of torsion spring 32 T1 (via the drive wheel 30), to slide along the slot 36. The vertical force component/needle insertion force V is absorbed and opposed by, the chassis 22 (via the force applied by the pin 34 on the slot 36). Therefore, for example, during extended storage of the injector 10 until use, wherein the chassis 22 and the injection needle 24 are required to be locked in the retracted position, the activation switch 38, which maintains the chassis 22 and the injection needle 24 in the retracted position, is exposed to less force than the full effect of the rotational force T1 of the rotary biasing assembly 28.

Further advantageously, the pin 34 may be positioned about the drive wheel 30 (during manufacturing) to minimize the magnitude of the horizontal force component H relative the magnitude of the vertical force component V of the rotational force T1 of the rotary biasing assembly 28. For example, the pin 34 may be positioned about the drive wheel 30 to have a greater vertical perpendicular distance Y1 from the center of rotation of the drive wheel 30 relative to the horizontal perpendicular distance X1 thereof from the center of rotation of the drive wheel 30, resulting in a smaller horizontal force component H relative to the vertical force component V (see FIG. 8: distance X1 relative to distance Y1). Accordingly, the resultant force H on the activation switch 38 is also less than the needle insertion force V, which minimizes the risk of damage to the activation switch 38, such as, for example, due to creep of a polymeric activation switch 38 or sticking of the pin 34 to the terminal end 40a of the activation switch 38. In one embodiment, the activation switch 38 may be constructed of a material having a stiffness greater than the material forming the pin 34 to further reduce the risk of activation switch 38 creep. Therefore, the activation switch 38 may be easily triggered, without having excessive forces applied thereon thereto during storage.

Figure 7:
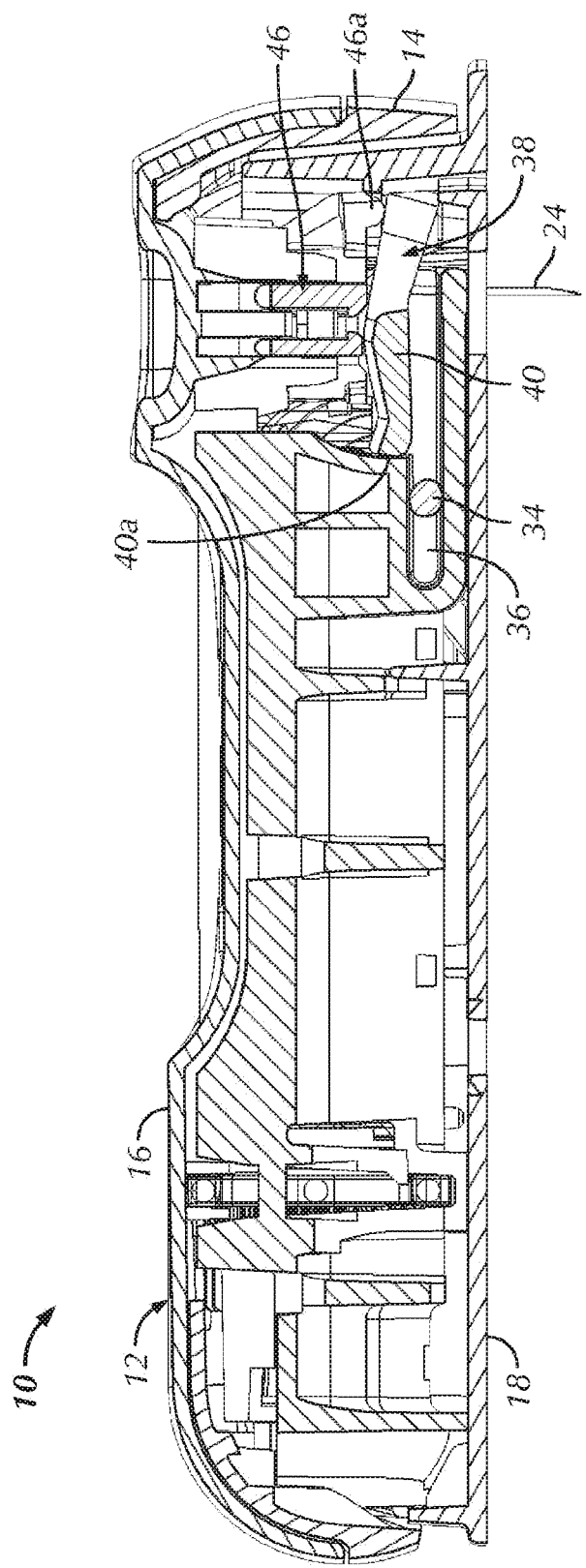
FIG. 7 is a cross-sectional, elevational view of the injector of FIG. 6, taken along the sectional line 7-7 of FIG. 6.

An activation button 46 is movably mounted to the injector housing 12, and is translatable (by a user) from an unactuated position (FIGS. 1-4, 8) to an actuated position (FIG. 7). As shown in FIG. 7, translation of the activation button 46 from the unactuated position thereof to the actuated position thereof engages the button with the activation switch 46 and rotates the activation switch 38 (about the pivot point 41) from the unactivated position thereof to the activated position thereof, and, in turn, triggers injection needle insertion. In the illustrated embodiment, and as shown best in FIGS. 4, 7 and 8, the activation button 46 includes a front lip 46a vertically aligned with the central portion 44 of the activation switch 38 (i.e., the front-most portion), whereby translation of the activation switch 46 from the unactuated position to the actuated position engages the lip 46a with the front end of the activation switch 38, effecting rotation of the activation switch 38 about the pivot point 41 thereof. As shown in the figures, the activation button 46 is translatable in a vertical direction, but one having ordinary skill would appreciate that the translation direction of the activation button 46 may be in any direction sufficient to engage and rotate the activation switch 38.

Figure 8:
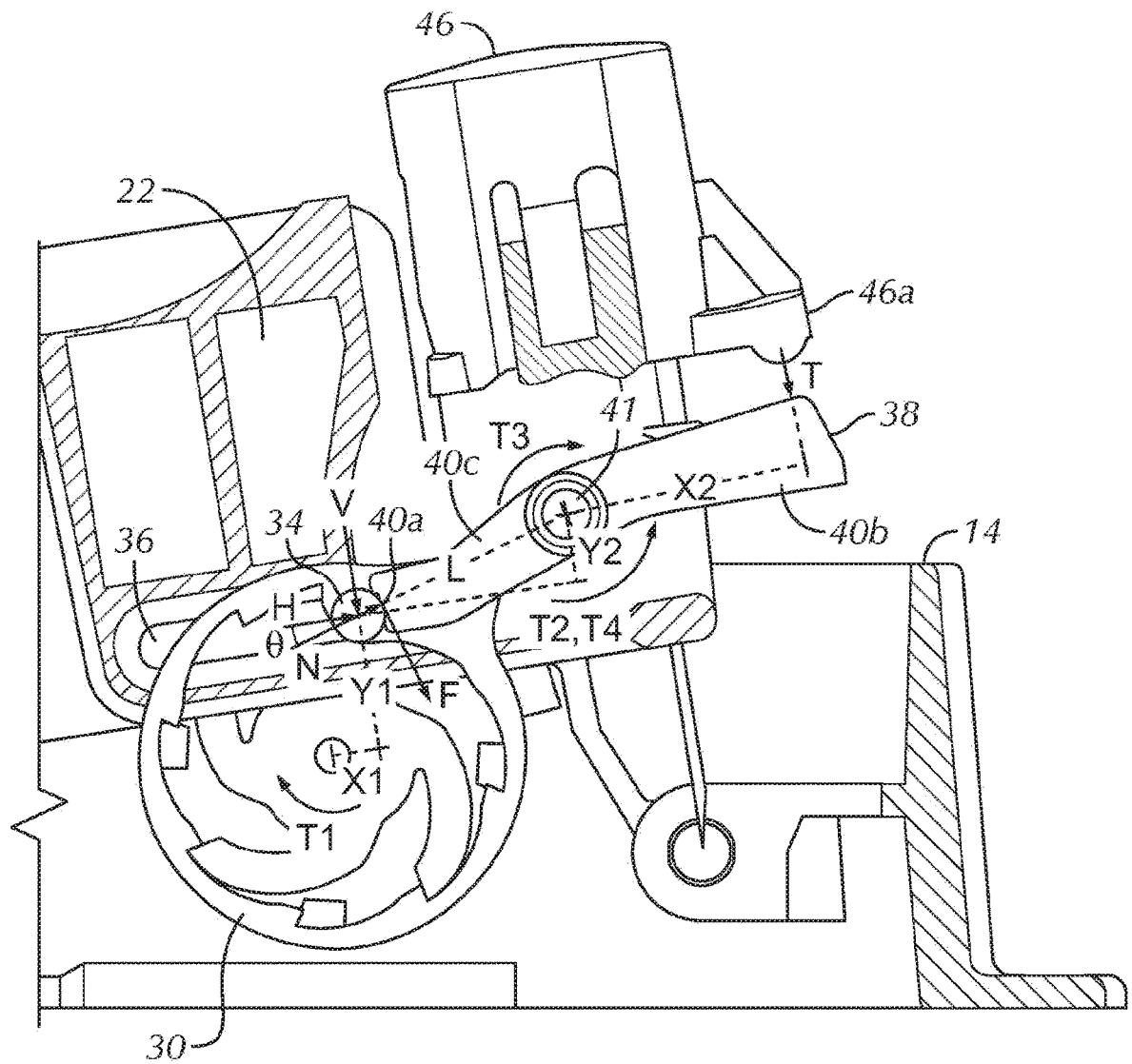
FIG. 8 is an enlarged, partial cross-sectional, elevational view of the injector of FIG. 1, taken along the sectional line 4-4 of FIG. 2.

Turning again to the activation switch 38, and as shown best in FIG. 8, the first arm 40 comprises a first segment 40b and an adjoining second segment 40c in series with the first segment 40b (the same applies for the second arm 42). The first segment 40b extends from the central portion 44 to the pin connection 41 and the second segment 40c extends from the pin connection 41 and terminates in the terminal free end 40a. As shown best in FIGS. 4, 7 and 8, the second segment 40c may be angled relative to the first segment 40b at the pin connection 41.

Advantageously, the geometry of the activation switch 38, the geometry of the activation button 46, the interface between the activation button 46 and the activation switch 38, the interface between the activation switch 38 and the rotary biasing assembly 28, and/or the materials of the activation switch 38 and components of the rotary biasing assembly 28 may be configured to achieve a desired activation feel by a user when depressing the activation button 46 to initiate injection needle insertion. That is, configuration of such features may adjust a pushing force (translational force T) on the activation button 46 required to rotate the activation switch 38 from the unactivated position thereof to the activated position thereof to initiate injection needle insertion.

For example (see FIG. 8), and as previously explained, the torque T1 applied by the torsion spring 32 on the pin 34 can be decomposed into a horizontal force component H applied onto the terminal end 40a of the first arm 40 and a vertical force component V applied onto the chassis 22. The magnitude of the horizontal force component H is equal to the torque T1 divided by the vertical perpendicular distance Y1 and the magnitude of the of the vertical force component V is equal to the torque T1 divided by the horizontal perpendicular distance X1. The horizontal force component H applies a threshold torque T2 upon the activation switch 38 about the pivot point 41 thereof, maintaining the activation switch 38 in the unactivated position thereof, and which must be overcome with a counter-torque T3 to rotate the activation switch 38 into the activate position thereof. The threshold torque T2 is equal, in part, to the magnitude of the force component H multiplied by the perpendicular vertical distance Y2. The counter-torque T3 is equal to the magnitude of the translational force T applied by the activation button 46 on activation switch 38 multiplied by the perpendicular horizontal distance X2.

As should be understood by those of ordinary skill in the art, therefore, the geometry of the activation switch 38 impacts the force V2 required by a user on the activation button 46 to move the activation button 46 from the unactuated position to the actuated position thereof, triggering injection needle insertion, i.e., rotating the activation switch 38 from the unactivated position to the activated position thereof, and, in turn, releasing the rotary biasing assembly 28 into the energy releasing state thereof to drive the chassis 22 and the injection needle 24 from the retracted position to the injection position thereof. For example, the angle of the second segment 40c relative to the first segment 40b of the first arm 40 impacts the vertical distance Y2 between the pin 34 and the pivot point 41, and, in turn, impacts the resultant threshold torque T2 produced by the horizontal force component H. Reduced threshold torque T2 reduces the required counter-torque T3, and, in turn, reduces the translational force T required by a user onto the activation button 46 to trigger injection needle insertion. Similarly, the distance between the pivot point 41 and the contact point of the activation button 46 with the activation switch 38 (the length X2) influences the required counter-torque T3. Therefore, engagement of the lip 46a with the central portion 44 of the activation switch 38, i.e., the forward-most portion of the activation switch 38, maximizes the length X2 to reduce the translational force T required by a user to achieve the required counter-torque T3 to initiate injection needle insertion. As should be understood by those of ordinary skill in the art, the aforementioned calculations are doubled in the illustrated embodiment to account for the rotational force T1 of two rotary biasing assemblies 28 imparted on the activation switch 38.

A force F of static friction opposing sliding of the terminal end 40a of the first arm 40 of the activation button 38 relative to the pin 34 may also factor into the translational force T required to move the activation button 46 from the unactuated position thereof to the actuated position thereof and trigger injection needle insertion. As should be understood by those of ordinary skill in the art, and as shown in FIG. 8, the friction force F is a tangentially directed force to the contact between the pin 34 and the terminal end 40*a* in a direction opposing movement of the activation switch 38 relative to the pin 34. As also should be understood, the magnitude of the friction force F is equal to the coefficient of static friction multiplied by the force N normal to the terminal end 40*a*. The force N is equal to the horizontal force component H of the pin 34 imparted on the terminal end 40*a* divided by the cosine of the included angle θ between the horizontal force component H and the normal force N (i.e., multiplied by the secant θ).

The friction force F applies a torque T4 on the pivot point 41 of the activation switch 38 equal to the friction force F multiplied by the perpendicular lever arm L. The torque T4, in addition to the torque T2, need be overcome by the user to move the activation button 46 from the unactuated position thereof to the actuated position thereof and trigger injection needle insertion. The lever arm L is substantially the length of the second segment 40*c* of the first arm 40*a*. The magnitude of the friction force F is affected by both the coefficient of static friction, as well as the angle of the face of the terminal end 40*a* relative to the horizontal force component H, i.e., affecting the angle θ. Therefore, for example, the materials forming the pin 34 and the activation switch 38, or the surface finish therebetween, may be selected to increase or decrease the friction force F in order to increase or decrease the translational force T required to be exerted by a user. Likewise, the angle of the face of the terminal end 40*a* may also be selected to increase or decrease the friction force F in order to increase or decrease the translational force T required to be exerted by a user. The length of the second segment 40*c* may also be selected to increase or decrease the translational force T required to be exerted by a user. As should be understood by those of ordinary skill in the art, the aforementioned calculations are doubled in the illustrated embodiment to account for the friction force F imparted on both the first and second arms 40, 42 of the activation switch 38.

Advantageously, therefore, the translational force T required to trigger injection needle insertion may be controlled by the rotational force T1 of the rotary biasing assembly 28, the friction force F. Moreover, the geometry of the activation switch 38 also influences the translational force T. For example, the ratio between the length of the first segment 40*b* relative to the second segment 40*c*, as well as the position of the pivot point 41, influences the translational force T. Further advantageously, adjusting the ratio between the rotational force T1 of the rotary biasing assembly 28 and the friction force F may also control how the translational force T changes during movement of the activation button 46 from the unactuated position thereof to the actuated position thereof.

As one non-limiting example, the translational force T may be adjusted to gradually decrease as the activation button is 46 is depressed. As another non-limiting example, the translational force T may be adjusted to sharply decrease as the activation button is 46 is depressed. Gradual change in force may give a user a feeling that the activation button 46 is progressing properly. Alternatively, a large initial force T that sharply decreases with movement of the activation button 46 may be advantageous to avoid the user from pushing half way and then stopping, i.e., once the button 46 starts moving it will not stop in the middle. The rotational force T1, due to the force of the torsion spring 32 and the changing rotational position of the pin 34 relative to the center pivot point of the drive wheel 30, may exhibit gradual change, whereas the friction force F, i.e., the difference between static friction and dynamic friction, may exhibit sharp change. Thus, the ratio of the rotational force T1 relative to the friction force F may adjust how the translational force T changes throughout depression of the activation button 46.

Figure 9:
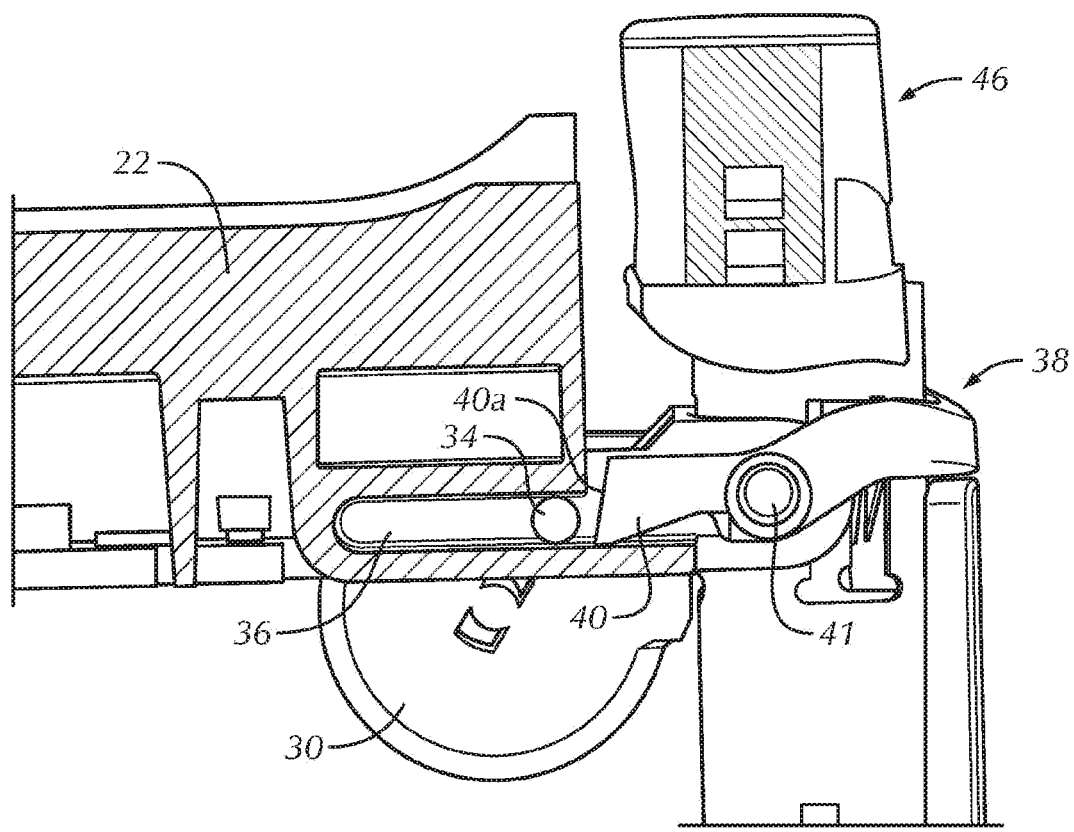
FIG. 9 is an enlarged, partial cross-sectional, elevational view of an alternative embodiment of FIG. 1, taken along sectional line 4-4 of FIG. 2.

Controlling the angle of the face of the terminal end 40*a* may also influence the translational force T. For example, as shown best in FIG. 8, the face of the terminal end 40*a* may be angled toward the base housing portion 14, i.e., with the direction of rotation of the activation switch 38 between the unactivated position thereof to the activated position thereof, thereby reducing the friction force F and more easily releasing the activation switch 38 from the pin 34. As also shown in FIG. 8, the bottom corner of the face of the terminal end 40*a* is gradually angled, e.g., curved. Therefore, the translational force T may be reduced gradually during release of the activation switch 38 from the pin 34. As another non-limiting example, and as shown in FIG. 9, the face of the terminal end 40*a* may alternatively be angled toward the chassis 22, i.e., against the direction of rotation of the activation switch 38 between the unactivated position thereof to the activated position thereof. Accordingly, the face of the terminal end 40*a* resists initial rotation of the activation switch 48 to the activated position thereof. For example, the face of the terminal end 40*a* must push the pin 34 back, i.e., in the opposite direction of the horizontal force component H, in order to initiate activation switch 38 rotation. Moreover, the friction force F is increased. For example, the angled face of the terminal end 40*a* may push the pin 34 upward against the slot 36, increasing friction. As also shown in FIG. 9, the bottom corner of the face of the terminal end 40*a* is sharply angled. Therefore, the translational force T may be reduced suddenly upon release of the activation switch 38 from the pin 34. Thus, the activation button 46 may initially require a large translational force T and then suddenly move with less translational force T until it reaches the actuated position thereof.

It will be appreciated by those skilled in the art that changes could be made to the embodiments described above without departing from the broad inventive concept thereof. It is understood, therefore, that this invention is not limited to the particular embodiment(s) disclosed, but it is intended to cover modifications within the spirit and scope of the present invention, as set forth in the appended claims.

We claim:

1. An injector comprising:
   a housing having a base housing portion defining a skin contact surface;
   a chassis attached to the base housing portion;
   an injection needle supported by the chassis, the injection needle being movable with the chassis relative to the base housing portion from a retracted position, wherein at least a tip of the injection needle is contained within the base housing portion, to an injection position, wherein at least the tip of the injection needle protrudes from the base housing portion;
   at least one rotary biasing assembly stabilized in a stored energy state and releasable into an energy releasing state, the at least one rotary biasing assembly including a cam;
   at least one cam follower corresponding to the at least one rotary biasing assembly, the at least one cam follower coupling the at least one rotary biasing assembly with the injection needle and being configured to transform rotation of the at least one rotary biasing assembly in the energy releasing state thereof into translation of the chassis and the injection needle, relative to the base housing portion, from the retracted position to the injection position;
an activation switch pivotably coupled with the chassis and rotatable from an unactivated position, stabilizing the at least one rotary biasing assembly in the stored energy state, to an activated position, releasing the at least one rotary biasing assembly into the energy releasing state; and
an activation button movably mounted to the housing, the activation button being translatable from an unactuated position to an actuated position, wherein a translation of the activation button from the unactuated position to the actuated position rotates the activation switch from the unactivated position to the activated position thereof.

2. The injector of claim 1, wherein the at least one rotary biasing assembly comprises a drive wheel and a torsion spring coupled thereto.

3. The injector of claim 2, wherein the drive wheel includes a toothed interior ratchet surface and a pawl engaged with the toothed interior ratchet surface, the pawl and the toothed interior ratchet surface being configured to permit rotation of the drive wheel in a single direction, and wherein the torsion spring is coupled to the pawl.

4. The injector of claim 2, wherein the torsion spring is wound in the stored energy state, and configured to unwind in the energy releasing state.

5. The injector of claim 2, wherein the at least one cam follower comprises a slot formed in the chassis, and wherein the cam of the at least one rotary biasing assembly comprises a pin projecting from the drive wheel into engagement with the slot.

6. The injector of claim 5,
wherein the engagement of the pin with the slot converts rotation of the drive wheel into a horizontal sliding of the pin along the slot and the translation of the chassis and the injection needle relative to the base housing portion from the retracted position to the injection position, and
wherein prevention of the horizontal sliding of the pin along the slot prevents rotation of the drive wheel and, in turn, prevents the translation of the chassis and the injection needle from the retracted position to the injection position.

7. The injector of claim 6, wherein the activation switch is generally U-shaped, and has a first arm with a terminal free end, a second arm with a terminal free end, and a central portion extending between the first arm and the second arm, wherein the first arm extends along one side of the chassis, the second arm extends along an opposing side of the chassis and the central portion extends around a front end of the chassis, and at least one of the first arm or the second arm is pivotably coupled with the chassis.

8. The injector of claim 7, wherein at least one of the terminal free end of the first arm or the terminal free end of the second arm abuts the pin in the unactivated position of the activation switch, preventing rotation of the drive wheel, and wherein the activation switch disengages the pin in the activated position thereof, thereby permitting rotation of the drive wheel.

9. The injector of claim 1, wherein the activation switch is generally U-shaped, and has a first arm with a terminal free end, a second arm with a terminal free end, and a central portion extending between the first arm and the second arm, wherein the first arm extends along one side of the chassis, the second arm extends along an opposing side of the chassis and the central portion extends around a front end of the chassis, and at least one of the first arm or the second arm is pivotably connected to the chassis.

10. The injector of claim 9, wherein:
the first arm comprises a first segment and a second segment that adjoins with the first segment in series, the first segment extending from the central portion and the second segment terminating in the terminal free end of the first arm, the second segment being angled relative to the first segment, and
the second arm comprises a first segment and a second segment that adjoins with the first segment of the second arm in series, the first segment of the second arm extending from the central portion and the second segment of the second arm terminating in the terminal free end of the second arm, the second segment of the second arm being angled relative to the first segment of the second arm.

11. The injector of claim 10, wherein:
the first arm is pivotably connected to the chassis at a first pivot point and the second segment of the first arm is angled relative to the first segment of the first arm at the first pivot point, and
the second arm is pivotably connected to the chassis at a second pivot point and the second segment of the second arm is angled relative to the first segment of the second arm at the second pivot point.

12. The injector of claim 1, wherein the at least one rotary biasing assembly comprises two rotary biasing assemblies, and the at least one cam follower comprises two cam followers.

13. The injector of claim 1, wherein the chassis is pivotably attached to the base housing portion proximate a rear end of the chassis and the base housing portion, and the activation switch is pivotably coupled with the chassis proximate a front end of the chassis.

14. The injector of claim 1, wherein the chassis is pivotably attached to the base housing portion.

15. The injector of claim 1, wherein in the unactivated position the activation switch is engaged with the cam to stabilize the at least one rotary biasing assembly in the stored energy state, and
wherein in the activated position the activation switch is disengaged form from the cam to release the at least one rotary biasing assembly into the energy releasing state.

16. An injector comprising:
a housing having a base housing portion defining a skin contact surface;
an injection needle supported by the housing, the injection needle being movable relative to the base housing portion from a retracted position, wherein at least a tip of the injection needle is contained within the base housing portion, to an injection position, wherein at least the tip of the injection needle protrudes from the base housing portion;
at least one rotary biasing assembly stabilized in a stored energy state and releasable into an energy releasing state, the at least one rotary biasing assembly including a cam;
at least one cam follower corresponding to the at least one rotary biasing assembly, the at least one cam follower coupling the at least one rotary biasing assembly with the injection needle and being configured to transform rotation of the at least one rotary biasing assembly in the energy releasing state thereof into translation of the injection needle, relative to the base housing portion, from the retracted position to the injection position;

an activation switch rotatable from an unactivated position, which the activation switch is engaged with the cam to stabilize the at least one rotary biasing assembly in the stored energy state, to an activated position, in which the activation switch is disengaged from the cam to release the at least one rotary biasing assembly into the energy releasing state; and an activation button movably mounted to the housing, the activation button being translatable from an unactuated position to an actuated position, wherein a translation of the activation button from the unactuated position to the actuated position rotates the activation switch from the unactivated position to the activated position thereof.

17. The injector of claim 16, wherein the at least one rotary biasing assembly comprises a drive wheel and a torsion spring coupled thereto.

18. The injector of claim 17, wherein the torsion spring is wound in the stored energy state, and configured to unwind in the energy releasing state.

19. The injector of claim 16, wherein the at least one rotary biasing assembly comprises two rotary biasing assemblies, and the at least one cam follower comprises two cam followers.

* * * * *